United States Patent
Jones et al.

(10) Patent No.: US 7,285,401 B1
(45) Date of Patent: Oct. 23, 2007

(54) METHOD AND REAGENTS FOR DETECTING NUCLEIC ACID SEQUENCES

(75) Inventors: Theodore Jones, Lakewood, CO (US); Rodney M. Richards, Broomfield, CO (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 08/480,005

(22) Filed: Jun. 7, 1995

Related U.S. Application Data

(63) Continuation of application No. 08/207,241, filed on Mar. 7, 1994, now abandoned, and a continuation of application No. 07/220,108, filed on Jun. 24, 1988, now abandoned.

(51) Int. Cl.
   *C12Q 1/00* (2006.01)
(52) U.S. Cl. .................. 435/91.2; 536/23.1; 536/24.3; 536/24.33; 536/25.3; 536/25.4; 435/91.1; 435/6

(58) Field of Classification Search .................. 435/6, 435/91.2, 191, 91.1; 536/24.3, 24.33, 25.3, 536/25.4, 23.1
See application file for complete search history.

(56) References Cited

OTHER PUBLICATIONS

Boehringer Mannhein Biochemicals 1992 catalog, p. 650.*

* cited by examiner

*Primary Examiner*—Bruce R. Campell
*Assistant Examiner*—Myron G. Hill
(74) *Attorney, Agent, or Firm*—Joan Eggert; MarySusan Howard; Kathleen Fowler

(57) ABSTRACT

The present invention is directed to a method for detecting an amplification product. Amplification is accomplished through the use of a plurality of detection probes. The present invention is also directed to a method for detecting a target nucleic acid sequence by contacting a test sample with an excess of at least three pairs of nucleic acid amplification probes.

25 Claims, 6 Drawing Sheets

Nucleotide Sequences Used in Examples 2-8

WHEREIN:

$AS_{1-3}$ and $AS_{1-3}'$ = target sequences in Examples 4-6
$AS_{1-2}$ and $AS_{1-2}'$ = target sequences in Examples 2, 3, and 8
$AP_1$, $AP_1'$, $AP_2$, $AP_2'$, $AP_3$, and $AP_3'$ = amplification probes in Examples 4-5
$AP_1$, $AP_1'$, $AP_2$, and $AP_2'$ = amplification probes in Examples 2-3
$DP_1$ and $DP_2$ = detection probes in Example 6
$DP_1'$ = detection probe in Example 8

Amplification of 30-mer Amplification Sequence
Using Two Pairs of Amplification Probes
and 10 Cycles of Amplification Amplification of 45-mer Amplification Sequence
Using Three Pairs of Amplification Probes
and 10 Cycles of Amplification Reaction I Reaction II Detection of 30-mer Amplification Product Using
One Labeled and One Non-labeled Detection Probe

METHOD AND REAGENTS FOR DETECTING NUCLEIC ACID SEQUENCES

This application is a continuation of U.S. Ser. No. 08/207,241 filed Mar. 7, 1994 now abandoned, which is a continuation of U.S. Ser. No. 07/220,108 filed Jun. 24, 1988 now abandoned.

BACKGROUND OF THE INVENTION

Advances in the field of molecular biology over the last two decades have enabled the detection of specific nucleic acid sequences in test samples taken from a patient or other subject. Such test samples include serum, urine, feces, tissue, saliva, cerebrospinal fluid, amniotic fluid, and other bodily fluids. Detection of specific nucleic acid sequences can be used to identify genetic disorders or diseases, as well as the presence of pathogenic bacterial and viral associated diseases in humans. The presence of specific genes can also be used to obtain other pertinent genetic information, such as the presence of genes coding for antigens responsible for graft rejection, as well as genetic information used in cancer and oncogene testing and in forensic medicine.

The most common techniques for detecting a particular gene sequence utilize a phenomenon known as nucleic acid hybridization. Hybridization refers to a particular type of recombination, or annealing, of a single-stranded nucleotide sequence with a complementary sequence to form a double-stranded nucleic acid, or duplex, through non-covalent bonding. Where the original strands of a normally double-stranded DNA (deoxyribonucleic acid) molecule recombine, the recombination process is referred to as renaturation. Where molecular mixing occurs, the process is referred to as hybridization. Hybridization can also occur with RNA (ribonucleic acid) which is frequently found in nature in both a double-stranded and a single-stranded form. DNA:RNA hybrids can be formed through hybridization, as well as DNA:DNA and RNA:RNA hybrids.

In typical hybridization techniques, a single-stranded probe sequence is used to seek out the gene or nucleic acid sequence of interest by annealing, or hybridizing, to the single-stranded form of the target nucleic acid sequence. Where the nucleic acid in a test sample is double-stranded, as is typically the case with naturally occurring DNA, the DNA must be denatured, or rendered single-stranded, before any form of recombination can take place. The target sequence is a selected portion of the nucleic acid sequence being sought which is uniquely characteristic of that target sequence. The probe is selected to be a single-stranded nucleotide sequence complementary to the target nucleotide sequence of the gene being sought. This oligonucleotide probe is marked with a detectable label and brought into contact with the denatured nucleic acid (DNA or RNA) from a test sample.

Until recently, radioactive isotopes of atoms such as hydrogen (3H), phosphorus ($^{32}$P), or iodine ($^{125}$I) were primarily used for probe labels. Radioactive compounds such as these, however, suffer from many drawbacks, including the necessity of incorporating extensive safety precautions into assay protocols, the need for expensive equipment and special waste treatment procedures, as well as high usage costs due to the instability of the radioactive materials. As a result, there have been increasing efforts in recent years to develop alternative labeling schemes not having the drawbacks of radioactive isotope labels. Consequently, non-isotopically labeled probes are currently used in addition to radioactive labels, although non-radioactive labels are preferred in a clinical setting.

DESCRIPTION OF THE PRIOR ART

In an effort to improve the detection of minute quantities of target sequences present in test samples, developments have recently been made in the areas of: (1) amplifying the signal, that is, increasing the sensitivity of the probe detection system; as well as, (2) amplifying the target nucleic acid sequence itself so that it is present in quantities sufficient to be readily detectable using currently available radioactive and non-radioactive methods. Amplification of the target nucleic acid sequence generally involves the repetitive reproduction or replication of the given DNA or RNA target nucleic acid sequence.

Two methods are currently used routinely for reproduction or replication to produce multiple copies of a nucleic acid sequence from a small quantity of a given existing target nucleic acid sequence. The first method involves the cloning of the target nucleic acid sequence into an appropriate host system. This method employs traditional cloning techniques wherein the desired nucleic acid is inserted into an appropriate vector which is subsequently used to transform the host. When the host is cultured, the vector is replicated, producing additional copies of the desired target nucleic acid sequence. The target nucleic acid sequence which is inserted into the vector can be either naturally occurring or synthesized. In other words, the desired target nucleic acid sequence can be synthesized in vitro and then inserted into a vector which is amplified by growth prior to each succeeding insertion, as disclosed in U.S. Pat. No. 4,293,652.

U.S. Pat. Nos. 4,683,195 and 4,683,202 disclose a second method for amplifying the amount of target DNA or RNA from a test sample. This particular method has been referred to as the polymerase chain reaction (PCR). PCR amplification utilizes two oligonucleotide primers which flank the DNA segment to be amplified. The primers anneal to their complementary sequences, on opposite strands of the target nucleic acid sequence, with extension products (complementary to the target sequence) of the annealed primers being formed in the presence of DNA polymerase. The primers are oriented so that DNA synthesis by the polymerase proceeds across and through the region between the primers, effectively doubling the amount of the target DNA segment flanked by the primers.

Cycles of heat denaturation of the DNA, annealing of the primers to their complementary sequences, and extension of the annealed primers with DNA polymerase are repeated until a sufficient quantity of the target nucleic acid sequence is produced to result in measurable signal in the assay of choice. Because the extension products are also complementary to and capable of binding primers, each successive cycle essentially doubles the amount of DNA synthesized in the previous cycle, resulting in exponential accumulation of the target nucleic acid sequence.

One disadvantage of the PCR amplification system is that it requires the use of an enzyme in order to achieve amplification. Enzymes exhibit an inherent lot-to-lot variation, in addition to the undesired presence of nuclease contaminants, and a relatively short shelf life. It would be advantageous to have an amplification system that can effectively amplify both DNA and RNA, and that is not confined to the use of an enzymatic method of amplification.

SUMMARY OF THE INVENTION

The present invention relates to a method for detecting a target nucleic acid sequence which may be present in a test sample. The method may employ both an amplification procedure and a detection procedure.

Amplification is accomplished through the use of a plurality of pairs of nucleic acid amplification probes, wherein the member probes of each pair of amplification probes are complementary to each other with at least one same hybridizing member of each pair of amplification probes also being complementary to a given portion of the target nucleic acid sequence, which acts as a template. The nucleic acid sequence of the hybridizing member of each pair of amplification probes is selected to be complementary to a different portion of the target nucleic acid sequence, with the hybridizing amplification probes essentially covering a designated length of the target sequence in a contiguous manner. The hybridizing amplification probes hybridize to the target sequence sufficiently adjacent to each other to enable the probes to be joined together.

Once the hybridizing amplification probes are joined, the completed amplification product can be separated by denaturation, and the process repeated with the remaining probes or with a new supply of probes. Cycles of heat denaturation of the ligated amplification product, annealing of the amplification probes to their complementary sequences, and ligation of the annealed probes are repeated until a sufficient quantity of the target nucleic acid sequence is produced to result in measurable signal in the selected assay.

Where three or more pairs of amplification probes are employed, the amplification product may be specifically detected using two or more detection probes wherein each detection probe is complementary to a portion of each of two adjacently situated amplification probe segments of the amplification product. The correctly assembled amplification product serves as a template in a manner similar to that served by the target nucleic acid sequence in the amplification procedure. Incorrectly assembled product cannot function as a template in this procedure. The detection probes hybridize to the amplification product sufficiently adjacent to each other to enable an interaction to take place between the hybridized detection probes. Selected detection probes are provided with a label for use in detecting the amount of correctly assembled amplification product.

DETAILED DESCRIPTION OF THE INVENTION

Figure 1:
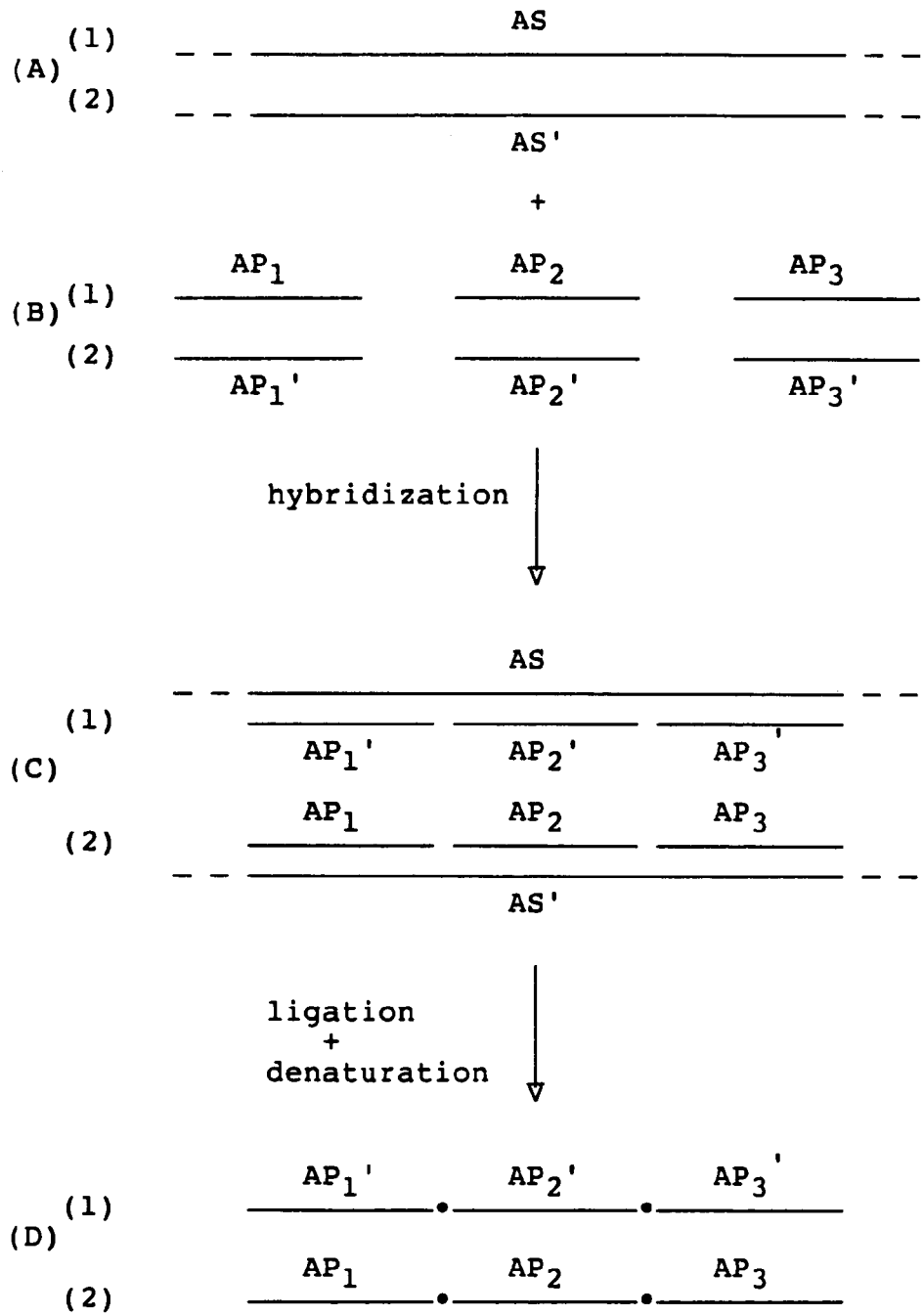
FIG. 1 is a diagram illustrating the amplification of a double-stranded target sequence using the amplification procedure of the present invention.

A method for detecting a target nucleic acid sequence which may be present in a test sample is provided in accordance with the present invention. The method of the present invention may employ both an amplification procedure and a detection procedure.

As used herein, the following terms have the definitions designated below.

Amplification Probe is a nucleic acid sequence which is either: (1) complementary to a portion of a single strand of a double-stranded amplification sequence; or, (2) complementary or identical to a portion of a single-stranded amplification sequence. The Amplification Probes hybridize to the amplification sequence sufficiently adjacent to each other to enable the probes to be joined together. Each Amplification Probe is greater than one nucleotide in length. The Amplification Probe may or may not be modified at one or both ends for joining to other Amplification Probes.

Nucleic Acid Sequence is a deoxyribonucleotide or a ribonucleotide which may be modified with respect to: (1) the phosphate backbone; (2) the nucleosides; and/or, (3) the sugar moiety of the oligonucleotide. Nucleic Acid Sequences can contain labels and can be interrupted by the presence of other chemical moieties, as long as hybridization is still able to occur.

Complementary refers to sufficient complementarity to enable hybridizing to occur. Complete complementarity is not required.

Same Member of a plurality of pairs of amplification probes refers to the member of each pair of probes which is cumulatively capable, with other "Same Members", of forming a complete amplification product. Members of amplification probe pairs are designated with the prime (') symbol where the designated member originates from the lower strand.

Amplification Product is the ligated nucleic acid sequence which is produced from the ligation of a series of amplification probes which are contiguously hybridized to an amplification sequence.

Ligation refers to the joining of two or more amplification probes or detection probes. Ligation includes enzymatic processes such as those utilizing a ligase, in addition to chemical processes, including, but not limited to, chemical reactions, photochemical reactions (e.g., photocoupling), thermocycloadditions, and redox reactions.

Contiguous is next to or near in proximity. In the case of contiguously hybridized probes, the ends of the probes need not abut against each other, but may in fact be either spaced apart or overlapping to some degree.

Target Sequence is the nucleic acid sequence being sought.

Amplification Sequence is a designated length of the target sequence which acts as a template for the amplification probes. The Amplification Sequence may comprise the entire length of the target sequence or a representative portion thereof.

Template Sequence is the nucleic acid sequence to which a plurality of amplification probes or a plurality of detection probes hybridize. In the first cycle of the amplification procedure, the amplification sequence acts as the Template Sequence. In subsequent cycles of the amplification procedure and in the detection procedure, amplification product also serves as a Template Sequence.

Amplification Probe Segment is that portion of an amplification product which originated with a single amplification probe.

Hybridizing Probe is an amplification probe or a detection probe which hybridizes to a template sequence. Generally, all amplification probes and all detection probes are Hybridizing Probes with the exception of certain amplification probes in the first cycle of the amplification of a single-stranded amplification sequence.

Detection Probe is a nucleic acid sequence which is complementary to a portion of each of two adjacently situated amplification probe segments in an amplification product. The Detection Probes hybridize to the amplification product sufficiently adjacent to each other to enable an interaction to occur between the hybridized probes.

Detection Product is the nucleic acid sequence which is produced from a series of contiguously hybridized detection probes. The Detection Product need not be ligated.

Spurious Amplification By-product, or By-product, is product, resulting from the ligation of amplification probes, which is not derived through the original amplification sequence(s).

Label is a moiety which is conjugated to a detection probe or amplification probe to distinguish like-labeled probes from other probes. The Label need not be a signal-producing label, but may, e.g., provide a means for separation of the product to be measured and/or a means for the subsequent attachment of a detectable label.

Detectable Label is a signal-producing label which is capable of detection either directly or through its interaction with a substance such as a substrate (in the case of an enzyme), a light source (in the case of a fluorescent compound), or a photomultiplier tube (in the case of a radioactive or chemiluminescent compound).

Proximity Label is one of at least two labels which interact with each other to produce a detectable signal where the proximity labels are brought together. Typically, a first Proximity Label is used in combination with a corresponding second Proximity Label in order to produce a detectable signal under conditions wherein the two Proximity Labels are proximate to each other.

An example of the amplification procedure of the present invention, employing a double-stranded amplification sequence, is depicted in FIG. 1. With reference to FIG. 1, the amplification procedure utilizes a plurality of pairs of amplification probes [(B)(1) and (B)(2)]. The amplification probes are preferably 10 to 30 nucleotides in length, but may be any length greater than one nucleotide. The members of each pair of amplification probes are selected to be complementary to each other, with at least one same member [(B)(1) or (B)(2)] of each pair of probes also being complementary to a designated segment of the amplification sequence [(A)(1) and (A)(2)], which acts as a template. The nucleic acid sequences of the hybridizing member of each pair of amplification probes is selected to be complementary to a different portion of the amplification sequence, such that the hybridizing amplification probes, when hybridized to the amplification sequence, essentially cover the entire length of the amplification sequence in a contiguous manner [(C)(1) and (C)(2)].

Where the amplification sequence is double-stranded, both members of each pair of amplification probes will necessarily be complementary to opposing portions of the complementary strands of the amplification sequence; i.e., amplification probes $AP_1$, $AP_2$, and $AP_3$ [(B)(1)] being complementary to the amplification sequence AS' [(A)(2)], and amplification probes $AP_1'$, $AP_2'$, and $AP_3'$ [(B)(2)] being complementary to the amplification sequence AS [(A)(1)].

The hybridizing amplification probes hybridize to the amplification sequence sufficiently adjacent to each other to enable the ends of the amplification probes to be ligated. One type of reaction capable of effecting ligation of the probes is the enzymatic action of a ligase on probes which have been phosphorylated at their 5'-ends. Other methods of ligation are also possible. Generally, these methods require the use of a ligating reagent, which may be a chemical, an enzyme (such as ligase), light, or heat.

In one embodiment, a single chemical moiety is attached to the joining ends of the amplification probes. Ligation may be effected by using a ligating reagent to produce the ligated amplification product through the formation of a second moiety. Preferably, the ligating reagent will only alter the structure of the first chemical moiety where two of the first chemical moieties are in close proximity, such as would be the case, for example, where two amplification probes tagged with the first chemical moiety are hybridized to a template. An example of utilizing a first chemical moiety to effect this type of ligation is the use of sulfhydryl groups (—SH) with ligation being achieved by oxidation to produce a disulfide linkage (—S—S—).

In another embodiment, a first chemical moiety is attached to a joining end of one amplification probe with a second chemical moiety being attached to the opposing end of another amplification probe to be ligated. Ligation is effected through the formation of a third chemical moiety, which may also be referred to as an altered first or second chemical moiety in some situations.

Ligation can be effected through the use of a ligating reagent in a manner similar to where only one chemical moiety is used to modify the joining ends of the probes. Where two different chemical moieties are used, the ligating reagent can interact with either the first or second chemical moiety, but it is preferred that the ligating reagent does not alter the structure of either chemical moiety unless and until the two chemical moieties are brought into close proximity, such as through hybridization. In the case where light is used as the ligating reagent, only one of the first two chemical moieties need interact with the light to produce an electrically excited molecule, which then reacts with the corresponding chemical moiety through a pericyclic reaction to produce the connecting third chemical moiety. It is preferred that the activated chemical moiety have a short-lived excited state so that it will react with the corresponding chemical moiety only where the two chemical moieties are in close proximity.

It is also possible to effect ligation in the absence of a ligating reagent where, for example, a nucleophile (N:) is attached to a joining end of one amplification probe with a leaving group being attached to the opposing end of another amplification probe to be ligated. Ligation occurs through the formation of the modified nucleophile (—N—). In this situation, ligation is effected simply by the close proximity (e.g., through hybridization) of N: and the selected leaving group. Alternatively, the leaving group may be activated by a reagent, such as light or an enzyme, to accelerate the ligation. An example of this type of ligation would be where N: is a sulfhydryl group, and the leaving group is the iodine on an iodo-acetyl group. This is similar to the type of chemistry used in the preparation of peptides and proteins where N: is an amine group and the leaving group is an active ester.

The use of the enzyme ligase as a ligating reagent to join a hydroxyl group (first chemical moiety) to a phosphate group (second chemical moiety) to produce a phosphate ester linkage (third chemical moiety), is a preferred method of ligation, because one of the two different chemical moieties necessary for ligation (i.e., the hydroxyl group) is endogenous to the nucleic acid probe. Where ligase is used to join phosphorylated probes, only one end of the probe need be modified.

Once the individual amplification probes are ligated, the resulting amplification products are separated, or rendered single-stranded, by denaturation of the amplification product [(D)(1) or (D)(2) in the case of a single-stranded amplification sequence, and (D)(1) and (D)(2) in the case of a double-stranded amplification sequence], and the process repeated with the remaining probes or with a new supply of amplification probes.

In the first repetition (second cycle) of the process, the amplification product itself acts as a template sequence for additional or residual amplification probes. For example, the amplification product formed from $AP_1'$, $AP_2'$, and $AP_3'$ [(D)(1)] acts as a template for the $AP_1$, $AP_2$, and $AP_3$ amplification probes [(B)(1)] in the second cycle of the amplification of a single-stranded amplification sequence. In the case of a double-stranded amplification sequence, the amplification product formed from $AP_1$, $AP_2$, and $AP_3$ [(D)(2)] would also act as a template for the $AP_1'$, $AP_2'$, and $AP_3'$ amplification probes [(B)(2)]. In subsequent cycles, both the (D)(1) and (D)(2) amplification products act as templates in the amplification of either a single-stranded or a double-stranded amplification sequence. The repeated production of additional amplification products, which act as templates in subsequent cycles, enables the exponential accumulation of amplification product.

The cycle of denaturation of the amplification product from the template sequence, annealing of additional or residual amplification probes to their complementary sequences on the template sequence, and ligation of the annealed amplification probes, is repeated until a sufficient quantity of the amplification product is produced to result in measurable signal in the assay of choice. Where heat denaturation is used, it is preferred to use a thermostable ligase.

The amplification product may be measured directly through the use of a commonly used two-step procedure involving: (1) denaturing polyacrylamide gel electrophoresis (PAGE) to separate (according to size) the amplification product from unligated and incompletely ligated residual amplification probes; followed by, (2) autoradiography to visualize the separated nucleic acid products. This procedure may be utilized where one or more of the amplification probes is labeled with a radioactive isotope such as $^{32}P$.

One of the problems inherent with the amplification procedure of the present invention is the potential production of spurious amplification by-products which may adversely affect assay results which are based on size separation, such as the two-step assay procedure described above. Spurious amplification by-products initially occur as the result of the ligation of amplification probes without benefit of the presence of a template sequence. This process, also known as blunt end ligation, can occur in solution where amplification probes, provided in excess for amplification of the amplification sequence, inadvertently align sufficiently proximate to each other to enable the probes to be ligated. Where spurious amplification by-products are produced from the ligation of both members of a complementary pair of amplification probes, the by-product is able to reproduce itself exponentially. Spurious amplification by-product is not indicative of the presence of the target sequence in the test sample under analysis.

The majority of spurious amplification by-products is oriented in a non-specific manner, due to the lack of initial participation by an amplification template to correctly align the probes. The detection procedure of the present invention is capable of discriminating between correctly and incorrectly assembled ligated product, and therefore minimizes, but does not completely eliminate, the effect of spurious amplification products on the final assay results. This is because discriminating methods, such as that of the present invention, still cannot distinguish between correctly ligated spurious amplification product and the correctly assembled true amplification product which is template-derived.

The deleterious effect of spurious amplification by-products can, however, be further minimized by the use of increasing numbers of pairs of amplification probes. Increasing the number of pairs of probes used in the amplification process statistically diminishes the opportunity for the probes to inadvertently align in the correct manner for spurious ligation. For example, taking into account only exponentially growing spurious amplification by-product, only one in sixteen of the spurious amplification products is calculated to be correctly assembled product formed in an amplification system using three pairs of probes. The ratio of correctly assembled spurious amplification product to the total spurious amplification product formed in an amplification system using four pairs of probes will be 1:352.

Reduction in the number of correctly assembled by-products increases dramatically with the inclusion of additional pairs of probes. For example, the ratio of correctly assembled by-product to total spurious amplification by product decreases to 1:13, 842 where five pairs of amplification probes are used. Additionally, the number of spurious amplification products that reach the full length of the template-derived amplification product will also diminish with increasing numbers of pairs of amplification probes.

At least two detection probes are used in accordance with the detection procedure of present invention. The detection probes are designed to span a junction of two amplification probe segments in a correctly assembled amplification product. Therefore, at least three pairs of amplification probes must be used in the amplification procedure of the present invention, in order to produce amplification product having at least three amplification probe segments. Preferably, the detection probes are comparable in length to the amplification probes.

Following sufficient cycling to generate a detectable quantity of amplification product, the correctly assembled amplification product may be detected in accordance with the detection procedure of the present invention. The amplification procedure produces two complementary amplification products, either or both of which may be detected in accordance with the detection procedure. An example of using the detection procedure of the present invention to detect the presence of one of the complementary amplification products is depicted in FIG. 2.

Figure 2:
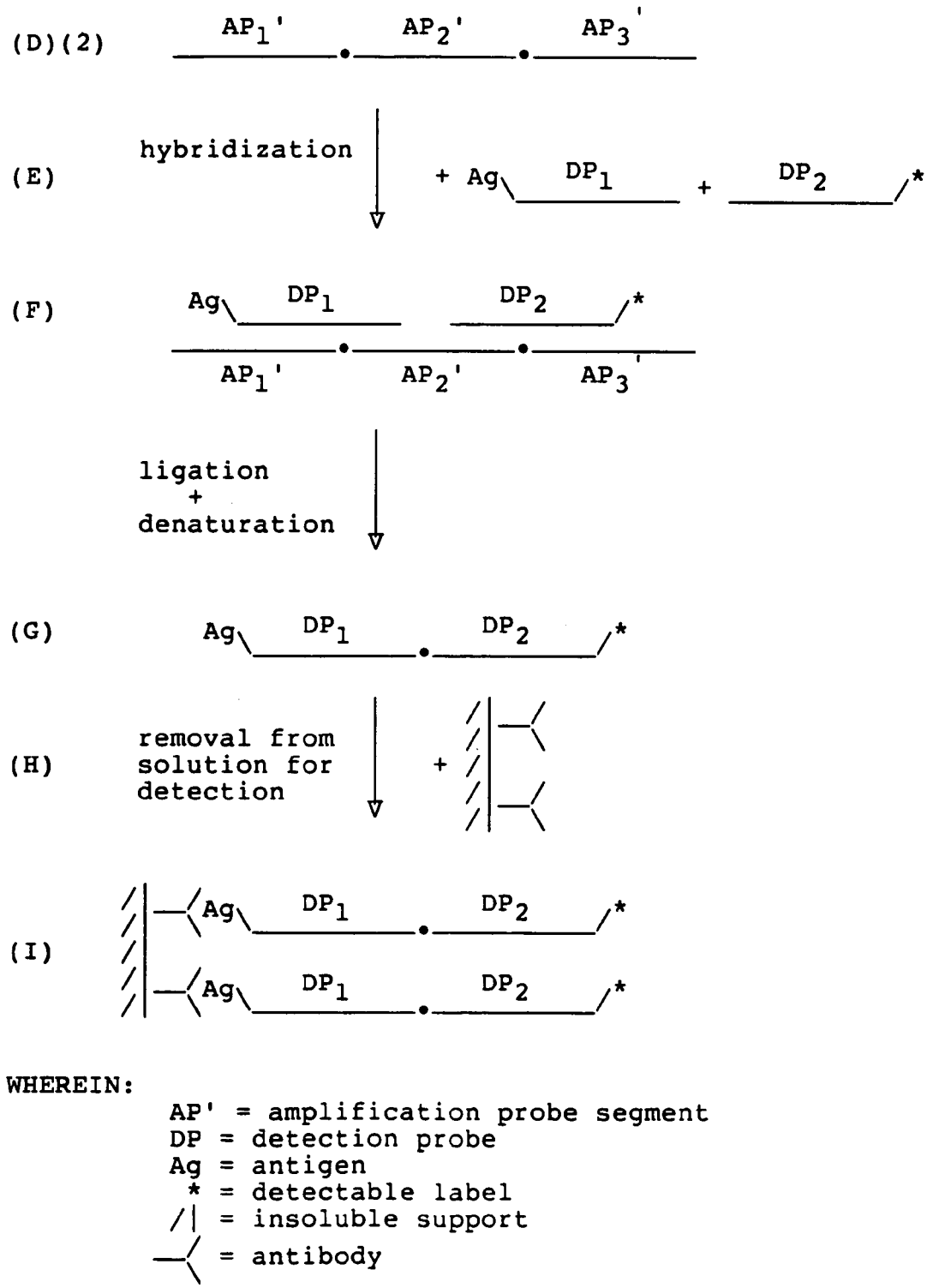
FIG. 2 is a diagram illustrating one embodiment of the detection procedure of the present invention using an antigen as a detection probe label to provide for subsequent separation of the detection product using immobilized antibody.

With reference to FIG. 2, the detection procedure of the present invention utilizes at least two detection probes [(E)] wherein each detection probe is complementary to a portion of each of two adjacently situated amplification probe segments of an amplification product. Preferably, where n pairs of amplification probes are used in the amplification procedure, n−1 detection probes are employed in the detection procedure.

In the detection procedure of the present invention, the amplification product [(D)(1) and/or (D)(2)] serves as a template in a manner similar to that served by the amplification sequence in the first cycle of the amplification procedure and by the amplification sequence and the amplification product in subsequent cycles. The detection procedure illustrated in FIG. 2 shows only one amplification product [(D)(1)], as a template sequence for the detection probes. The detection probes hybridize to the designated amplification product sufficiently adjacent to each other [(F)] to enable an interaction to occur between the hybridized probes. The interaction may be a ligating reaction which joins together the ends of the detection probes in any manner such as earlier described in connection with the ligation of amplification probes. Where a ligated detection product is formed [(G) in FIG. 2], the ligated product may subsequently be separated from the amplification product template by denaturation, although separation is not essential.

Any means of detection may be utilized which requires the presence of a correctly assembled detection product. Where one detection probe is labeled with $^{32}$P, the presence of ligated detection product may be assayed using PAGE followed by analysis with an autoradiogram. Where two detection probes are employed, each of the two detection probes may be provided with a label.

In one embodiment employing two labeled detection probes, one detection probe is conjugated to a detectable label with the other detection probe being provided with a means for removing the detection product from solution, such as a ligand which subsequently binds to its corresponding immobilized specific binding partner. In the detection procedure shown in FIG. 2, one of the detection probes is conjugated to an antigen which subsequently provides for removal of the detection product through the use of immobilized antibody [(H)]. The detection product may then be removed from solution by capturing the detection product onto an insoluble support [(I)]. This method of removing the labeled detection product from solution may also take place while the detection product is still hybridized to the amplification product.

In another embodiment, a first detection probe is conjugated to a first proximity label with a second detection probe being conjugated to a corresponding second proximity label. The labeled detection probes hybridize sufficiently adjacent to each other to enable the two proximity labels to interact with each other to produce a detectable signal. For example, the first proximity label may be a first enzyme which produces a product which serves as a substrate for a second enzyme. The second enzyme is conjugated to the second detection probe as a second proximity label. Where the two enzyme-labeled detection probes are brought into proximity, the second enzyme acts upon the product from the first enzyme, before the product can escape into bulk solution, to generate a second product which can be detected.

Alternatively, an energy donor, such as a fluorescent or chemiluminescent compound, may be used as one proximity label, with an energy acceptor, such as rhodamine being utilized as the second proximity label. Where the two labeled detection probes are brought into proximity, an energy transfer reaction takes place between the two proximity labels resulting in measurable energy emission. Still other methods for measuring the amount of detection product formed will be apparent to those skilled in the art.

The detection procedure is designed to depend upon the presence of amplification product to serve as a template for bringing the detection probes together. It is, however, possible for a single unligated amplification probe (for example, AP$_2$' in FIG. 2) to be capable alone of joining together the two detection probes, where the unligated amplification probe is complementary to portions of both of the detection probes. This phenomenon may be referred to as a "bridging" effect. It is therefore preferred to restrict the length of the AP$_2$' probe so that the degree of overlap of the unligated AP$_2$' probe with the detection probes is minimized. This decreases the propensity of the unligated AP$_2$' probe alone to form the "bridge" joining two detection probes. Elevated temperatures, lower ionic strength buffers, and/or denaturing agents such as formamide and urea, may be used in the ligation reaction as an alternative to short amplification probes in order to minimize formation of detection product through the "bridging" effect.

The detection procedure is relatively simple to use in combination with the amplification procedure. The detection procedure requires only two additional probe reagents and one additional cycle of hybridization. Hybridization of the detection probes may be followed by ligation, in some instances, as well as an optional denaturation step, depending upon the particular assay selected. Subsequent immobilization onto a solid support is rapid and requires little hands-on time.

The present invention is particularly advantageous because of its unique ability to allow for the adjustment of a multitude of parameters in order to tailor the selected procedure to achieve maximum sensitivity in the particular assay of choice. For example, the number of pairs of amplification probes can be adjusted to improve the sensitivity of an assay utilizing the amplification procedure of the present invention in combination with the two-step procedure of PAGE followed by autoradiography.

Additional parameters are made available for manipulation by using the detection procedure in combination with the amplification procedure of the present invention. Where both the amplification and detection procedures are incorporated into the same method, the effect of unintentional production of spurious amplification by-product is greatly minimized by taking advantage of the discrimination ability of the detection method while using increasing numbers of pairs of amplification probes.

The reagents of the present invention (amplification probes and detection probes) may be synthesized using any one of a number of available prior art methods for oligonucleotide synthesis known to those skilled in the art. One preferred method is a four-step procedure using commercially available reagents and an automated synthesizer. This four-step procedure involves: (1) deprotection of a polymer-bound protected starting nucleoside (first nucleic acid in sequence); (2) condensation of the deprotected starting nucleoside with a protected nucleoside phosphoramidite (second nucleic acid in sequence); (3) capping of the unreacted 5'-hydroxyl groups of the nucleosides; followed by, (4) oxidation of the newly formed phosphite bond.

These four steps are subsequently repeated to add further nucleic acids to the partially synthesized polymer-bound oligonucleotide sequence until the desired nucleotide is completed. In each repetition of the process, the last added nucleoside phosphoramidite becomes the starting nucleoside in the next cycle.

In order to extract the final synthesized oligonucleotide chain from the polymer, the resultant oligonucleotide must first be cleaved from the polymer which served as an anchor for synthesis. Separation of the oligonucleotide may be effected by treatment with fresh concentrated ammonia at room temperature. After decanting the oligonucleotide solution from the polymer, the concentrated ammonia solution is typically heated in a sealed tube for an extended period of time to remove the nucleoside protecting group.

The oligonucleotide solution may then be extracted with organic solvents such as 1-butanol and ethyl ether with the optical density of each solution being determined spectrophometrically at 260 nm to determine the concentration of the synthesized oligonucleotide. The oligonucleotide solutions may then be dried down for purification and desalting using known methods of preparative electrophoresis or column chromatographic methods.

Where a ligase is used to join hybridized probes, the amplification probes and detection probes may be phosphorylated using any of the available known methods. One preferred method is the polynucleotide kinase-catalyzed incorporation of phosphorus. Another preferred method is through chemical synthesis while the oligonucleotide probe still anchored to the synthesis polymer, prior to removal of the oligonucleotide from the support. The use of radioactive phosphorus for the phosphorylation also provides a means for subsequent visualization of the amplification products by autoradiography; i.e., through a radioactive label.

The probes of the present invention may also be provided with other labels in accordance with any of the known methods for attaching these labels. For example, nucleic acid probes may be labeled with fluorescein at their 5'-ends using a two-step process, wherein an amine group is first attached during synthesis. After removal of the oligo-amine from the support, fluorescein is attached to the amine-modified oligonucleotide using a solution of FITC (fluoroescein isothiocyanate) in DMSO (dimethylsulfoxide).

EXAMPLE 1

Preparation of Oligonucleotide Sequences

Figure 3:
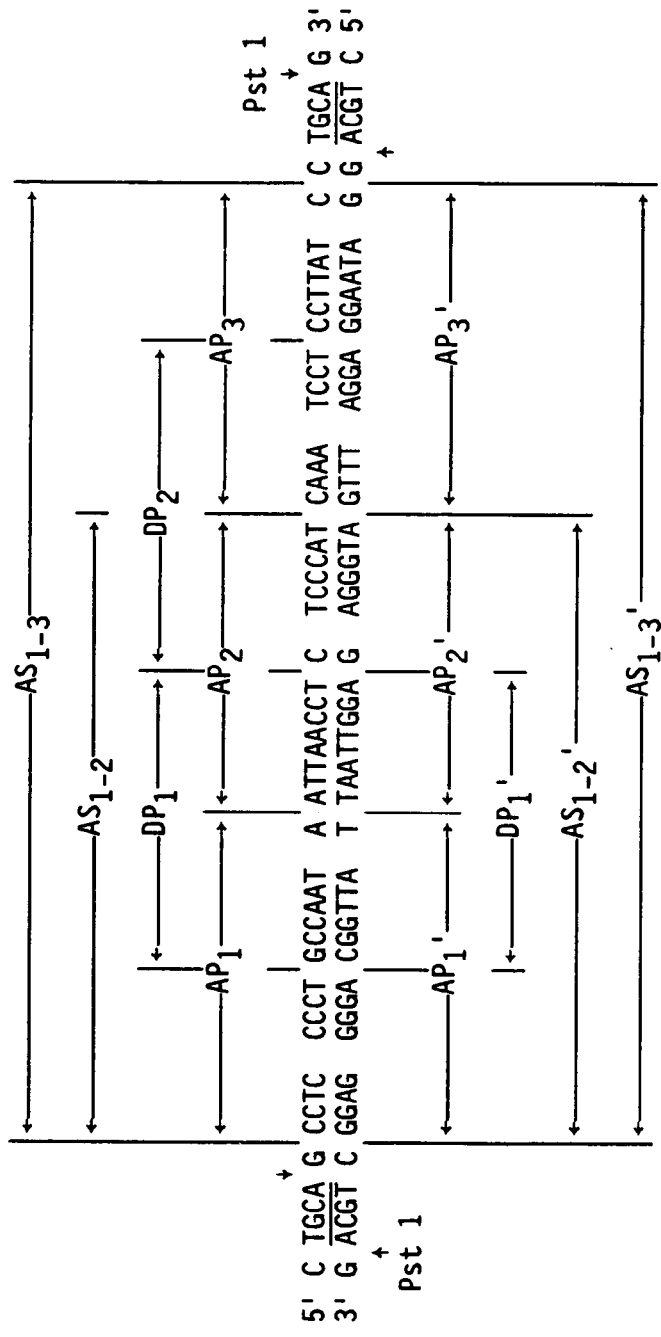
FIG. 3 is a diagram of the synthetic nucleotide sequences used in Examples 2-8.

In order to demonstrate the efficacy of the present invention, several different synthetic amplification sequences were used. The synthetic amplification sequences are contained within a 51 base pair Pst 1 fragment of HTLV-I, as displayed in FIG. 3. Amplification probes and detection probes were also synthesized to correspond to the nucleic acid sequences shown in FIG. 3.

All oligonucleotide sequences (amplification probes, detection probes, and synthetic amplification sequences) were synthesized using a four-step procedure with several intermediate washes, as set forth below. Syntheses were performed on an Applied Biosystems, Inc. (ABI, Foster City, Calif.) Model 380 automated synthesizer using commercially available reagents.

Polymer-bound dimethoxyltrityl-protected nucleoside (first nucleic acid in sequence) in support columns was first stripped of its 5'dimethoxytrityl protecting group by passing a solution of 3% trichloroacetic acid in dichloromethane through the column for one minute. The polymer was then washed with acetonitrile, followed by rinsing with dry acetonitrile. The polymer, containing the deprotected nucleoside, was then placed under argon prior to proceeding to the next (condensation) step.

The condensation step was carried out by first treating the polymer with tetrazole in acetonitrile. The polymer-bound deprotected nucleoside was then reacted with a protected cyanoethyl nucleoside phosphoramidite (second nucleic acid in sequence; ABI, Foster City, Calif.) in acetonitrile. The condensation reaction was allowed to proceed for 2.0 minutes, with the reactants being subsequently removed by filtration.

Condensation was followed by capping the unreacted 5'-hydroxyl groups of the nucleosides by passing a solution prepared by mixing one part of a mixture available from ABI (Foster City, Calif.) containing acetic anhydride and 2,6-lutidine in THF (tetrahydrofuran) and one part 1-methylimidazole in THF (also available from ABI, Foster City, Calif.) through the column for one minute.

Following removal of the capping solution, the polymer was treated for 1.5 minutes with an oxidizing solution (0.1 M $I_2$ in $H_2O$/2,6-lutidine/THF, 1:10:40). This was followed by an acetonitrile rinse. The cycle began again with a trichloroacetic acid/methylene chloride deprotection and was repeated until the desired oligonucleotide sequence was obtained.

The polymer-bound final oligonucleotide chain was treated with fresh concentrated ammonia at room temperature for 2.0 hours. After decanting the solution from the polymer, the concentrated ammonia solution was heated at 60° C. for 16 hours in a sealed tube.

Each oligonucleotide solution was extracted with 1-butanol and ethyl ether. The concentration of each extracted solution was determined spectrophometrically by measuring absorption at 260 nm. An aliquot of each extracted solution containing 5.0 O.D. units of synthesized oligonucleotide was concentrated for preparative electrophoresis and loaded into a 15% polyacrylamide 7 molar urea gel. After electrophoresis, the product band was visualized by U.V. shadowing, cut from the gel, extracted with elution buffer (300 mM-sodium acetate (NaOAc) 2.5 mM EDTA, 100 mM Tris-HCl, pH 8.0), and then desalted on a G-50 Sephadex® (Pharmacia LKB Biotech, Inc., Piscataway, N.J.) column using TEAB eluant (triethyl ammonium bicarbonate) to yield the purified oligonucleotide.

EXAMPLE 2

5 Cycles of Amplification with 2 Pairs of Probes

Two reactions were set up to evaluate the efficiency of the amplification procedure following five cycles of amplification using two pairs of amplification probes and enzymatic ligation. The variable reactants were established as follows:

Amount of Amplification Sequence

Reaction I: 10 fmoles each $AS_{1-2}$ and $AS_{1-2}'$
Reaction II: no amplification sequence
Additional reagents:

*E. Coli* DNA ligase buffer (ELB) was prepared at 10× concentration to contain 500 mM Tris-HCl (pH 8.0), 40 mM $MgCl_2$, 10 mM EDTA (ethylenediaminetetraacetic acid), 50 mM DTT (dithiothreitol), and contained 500 µg/ml BSA (bovine serum albumin).

Ligase/NAD β-nicotinamide-adenine-dinucleotide) reagent was prepared at 1× concentration in ELB to contain 130 µM NAD, with 2 µL of the reagent containing 1.6 units of *E. coli* Ligase (Boehringer Mannheim Biochemicals, Indianapolis, Ind.). This reagent was stored on wet ice for the duration of the amplification cycles.

EDTA/dye reagent was prepared to contain 11.8 mM EDTA, 6.3 M urea, 0.02% bromophenol blue, and 0.02% xylene cyanole.

Amplification probes $AP_1'$ and $AP_2$ were phosphorylated with $\gamma^{32}$P-ATP (adenosine-5'-triphosphate), adjusted (with cold phosphorus) to have a specific activity of approximately 700 Ci/mmole, and polynucleotide kinase (Boehringer Mannheim Biochemicals, Indianapolis, Ind.). The use of radioactive phosphorus for the phosphorylation satisfied a dual role of: (1) phosphorylating the ends of the amplification probes necessary for ligation to form the amplification product; and, (2) providing a means for subsequent visualization of the amplification products by autoradiography.

Each of the reaction mixtures was started in a volume of 13 µl in screw-top 1.5 ml polypropylene microtubes with rubber O-rings. (Sarstedt, Inc., Princeton, N.J.), 1.15× in ELB, and also contained 1.5 picomoles each of amplification probes $AP_1$, $^{32}P$-$AP_1'$, $^{32}P$-$AP_2'$ and $AP_2'$, in addition to the amount of amplification sequence designated above.

Reactions I and II were subjected to five cycles of amplification, as follows:

1. The polypropylene microtubes were sealed, clamped in a test tube rack, and then submerged in a 90° C. water bath for 5 minutes.
2. The reaction tubes were then removed from the water bath and allowed to sit at room temperature for five minutes, after which the tubes were spun briefly (several seconds) in an eppendorf micro centrifuge.
3. Two (2.0) µL of ligase/NAD reagent were added to each tube and the contents mixed by light agitation. Ligation was allowed to proceed for 5 minutes at room temperature to complete the amplification cycle.
4. The polypropylene microtubes were again spun briefly in an eppendorf micro centrifuge, with steps 1-3 being repeated four times to complete five cycles of amplification.

The reactions were quenched after the last cycle by adding 23 µL of EDTA/dye reagent. The quenched reaction mixtures were then incubated at 90° C. for 5 minutes and then quick chilled on ice. The resulting products from amplification were analyzed electrophoretically by running the samples on a denaturing 15% polyacrylamide gel (PAGE) using standard techniques known in the art, and visualized by autoradiography of the radio-labeled products.

Reaction efficiencies were estimated by comparing the amount of the remaining 15-mer unligated amplification probes to the resulting 30-mer amplification products as determined by integrating the signals by scanning laser densitometry with an UltroScan™ XL laser densitometer (Pharmacia LKB Biotech, Inc., Piscataway, N.J.).

Reaction I produced 145 femtomoles of 30-mer amplification product from the original amount of 10 femtomoles of starting amplification sequence, yielding a 14.5-fold amplification out of a theoretically possible 32-fold amplification, or an average efficiency of 71% per cycle.

No 30-mer amplification product was detected in Reaction II (control with no starting amplification sequence $AS_{1-2}$ and $AS_{1-2}'$).

EXAMPLE 3

10 Cycles of Amplification with 2 Pairs of Probes

Two reactions were set up to evaluate the efficiency of the amplification procedure following ten cycles of amplification using two pairs of amplification probes and enzymatic ligation. The variable reactants were established as follows:

Amount of Amplification Sequence

Reaction I: 1 fmole each $AS_{1-2}$ and $AS_{1-2}'$
Reaction II: no amplification sequence
Additional reagents:

E. Coli DNA ligase buffer (ELB), Ligase/NAD reagent, and EDTA/dye reagent were prepared the same as in Example 2.

Amplification probes $AP_1'$ and $AP_2$ were phosphorylated with $\gamma^{32}P$-ATP and polynucleotide kinase (Boehringer Mannheim Biochemicals, Indianapolis, Ind.) at a specific activity of approximately 700 Ci/mmole.

Each of the reaction mixtures was started in a volume of 13 µl in screw-top polypropylene microtubes, 1.15× in ELB, and also contained 2.0 picomoles each of amplification probes $AP_1$, $^{32}P$-$AP_1'$, $^{32}P$-$AP_2$, and $AP_2'$, in addition to the amount of amplification sequence designated above.

Reactions I and II were subjected to ten cycles of amplification following the procedure set forth in Example 2, with the exception that steps 1-3 were repeated nine times.

Figure 4:
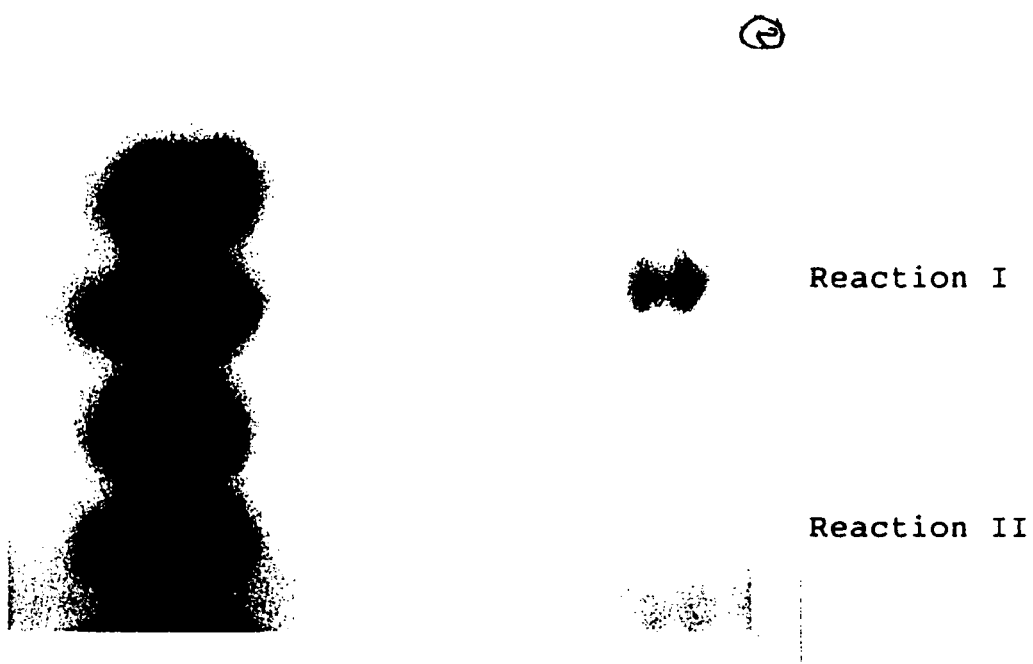
FIG. 4 is an autoradiogram illustrating the products resulting from 10 cycles of amplification of a 30-mer amplification sequence using two pairs of amplification probes.

The reactions were quenched after the last cycle by adding 33 µL of EDTA/dye reagent, followed by heating to 90° C. for 5 min., and subsequent quick chilling on ice. The resulting products were analyzed by running the reaction mixtures on denaturing 15% PAGE and then visualized by autoradiography. (FIG. 4). Product yields were determined by comparing the relative intensity of the 30-mer amplification products to the remaining 15-mer amplification probes as determined by the integrated signals from scanning laser densitometry. (Note: there are two 30-mer bands due to the different base composition of the two resulting strands $AS_{1-2}$ and $AS_{1-2}'$.)

Reaction I yielded 288 femtomoles of 30-mer amplification product from the original amount of 1 femtomole of starting amplification sequence. The 288× amplification achieved was calculated to represent an overall average efficiency of 76%.

The autoradiogram of Reaction II (the no amplification sequence control) revealed no detectable 30-mer amplification product after one hour of exposure. An overnight (16 hours) autoradiogram did, however, show a trace amount of 30-mer product in Reaction II, indicating product formation from blunt ligation in the absence of amplification sequence. The amount of this product was estimated from scanning laser densitometry to be approximately 14 femtomoles.

EXAMPLE 4

5 Cycles of Amplification with 3 Pairs of Probes

Two reactions were set up to evaluate the efficiency of the amplification procedure following five cycles of amplification using three pairs of amplification probes and enzymatic ligation. The variable reactants were established as follows:

Amount of Amplification Sequence

Reaction I: 5 fmole each $AS_{1-3}$ and $AS_{1-3}'$
Reaction II: no amplification sequence
Additional reagents:

E. Coli DNA ligase buffer (ELB) and EDTA/dye reagent were prepared the same as in Example 2.

Ligase/NAD reagent was prepared at 1× concentration in ELB to contain 130 µM NAD, with the concentration of E. coli Ligase (ICN Biomedicals, Inc., Costa Mesa, Calif.) being 25 units/µL. This reagent was stored on wet ice for the duration of the amplification cycles.

In this instance, amplification probes $AP_1'$, $AP_2$, $AP_2'$, and $AP_3$ were phosphorylated by introducing a nonradioactive phosphoryl group at the 5'-terminus, with the radioactive label used to visualize the resulting products after amplification by PAGE autoradiography being provided for by alternate means. The nonradioactive phosphoryl group was chemically introduced to amplification probes $AP_1{}^1$, $AP_2$, $AP_2{}'$, and $AP_3$ while the probes were still on the synthesis resin prior to deprotection of the nucleotides using 5'-Chemical Phosphorylating Reagent (Glen Research Corporation, Herndon, Va.). Horn, T. et al., *Tetrahedron Let.*, 27, 4705 (1986).

In order to provide a means for subsequent visualization of the amplification products by autoradiography, amplification probes $AP_1$ and $AP_3{}'$ were phosphorylated with $\gamma^{32}P$-ATP and polynucleotide kinase (Boehringer Mannheim Biochemicals, Indianapolis, Ind.) using radioactive phosphorus at a specific activity of approximately 7000 Ci/mmole. Phosphorylation was followed by dilution of the $^{32}P$-AP and $^{32}P$-$AP_3{}'$ probes with unphosphorylated $AP_1$ and $AP_3{}'$ probes, at a ratio of 1:10, to a achieve the desired final specific activity of 700 Ci/mmole. The radioactive probes were prepared in this manner to minimize the participation of their 5'-ends in the blunt end assembly of random products in the absence of amplification sequence; i.e., only 1 in 10 of the $AP_1$ and $AP_3{}'$ probes are phosphorylated and therefore capable of participating in a ligation event.

Each of the reaction mixtures was started in a volume of 8 μl in screw-top polypropylene microtubes, 1× in ELB, and also contained 1.0 picomole each of amplification probes $^{32}P$-$AP_1$, P-$AP_1{}'$, P-$AP_2$, P-$AP_2{}'$, P-$AP_3$, and $^{32}P$-$AP_3{}'$ in addition to the amount of amplification sequence designated above.

Reactions I and II were subjected to five cycles of amplification, as described in Example 2.

Following the last amplification cycle, the reactions were quenched by adding 18 μL of EDTA/dye reagent. This, in turn, was followed by heating the quenched reaction mixtures at 90° C. for 5 minutes, and then quick chilling on ice. The contents of each reaction tube were then run on denaturing 15% PAGE, with reaction products being visualized by autoradiography. Yields were estimated from the ratio of remaining 15-mer amplification probes to ligated 45-mer amplification products as quantitated by scanning laser densitometry.

Reaction I produced 64.5 femtomoles of 45-mer amplification product from 5 femtomoles of starting amplification sequence for a 12.9-fold amplification, or an average of 67% efficiency per cycle. Reaction II revealed no 45-mer products even after overnight autoradiography.

EXAMPLE 5

10 Cycles of Amplification with 3 Pairs of Probes

Two reactions were set up to evaluate the efficiency of the amplification procedure following ten cycles of amplification using three pairs of amplification probes and enzymatic ligation. The variable reactants were established as follows:

Amount of Amplification Sequence

| Reaction I: | 2 fmole each $AS_{1-3}$ and $AS_{1-3}{}'$ |
| Reaction II: | no amplification sequence |

Additional reagents:

*E. Coli* DNA ligase buffer (ELB) and EDTA/dye reagent were prepared the same as in Example 2.

Ligase/NAD reagent was prepared at 1× concentration in ELB to contain 130 μM NAD, with the concentration of *E. coli* Ligase (New England Biolabs, Inc. Beverly, Mass.) being 1 unit/μL. This reagent was stored on wet ice for the duration of the amplification cycles.

All amplification probes were phosphorylated as described in Example 4.

Each of the reaction mixtures was started in a volume of 8 μl in screw-top polypropylene microtubes, 1× in ELB, and also contained 1.0 picomole each of amplification probes $^{32}P$-$AP_1$, P-$AP_1{}'$, P-$AP_2$, P-$AP_2{}'$, P-$AP_3$, and $^{32}P$-$AP_3{}'$ in addition to the amount of amplification sequence designated above.

Both reactions were subjected to ten cycles of amplification, as described in Example 3, After the last cycle, the reactions were quenched by adding 28 μL of EDTA/dye reagent, followed by heating at 90° C. for 5 minutes, and subsequent quick chilling on ice.

Figure 5:
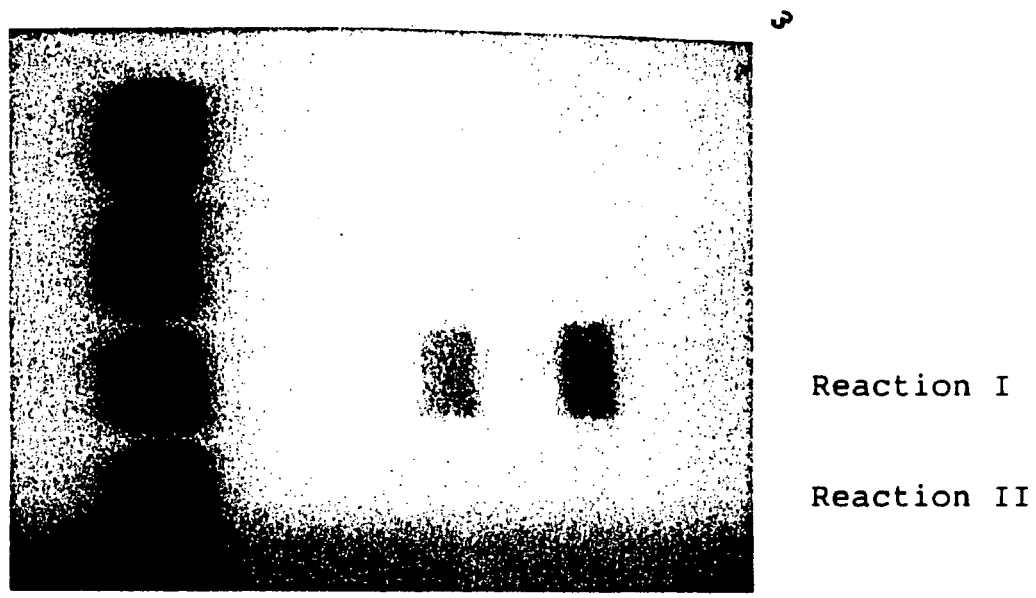
FIG. 5 is an autoradiogram illustrating the products resulting from 10 cycles of amplification of a 45-mer amplification sequence using three pairs of amplification probes.

The reaction mixtures were run on denaturing 15% PAGE, followed by visualization of products using autoradiography (FIG. 5). Reaction I produced 244 femtomoles of 45-mer amplification products as determined by the scanning laser densitometry technique described earlier. This 122× amplification corresponds to an overall average efficiency of 62% per cycle.

Overnight autoradiography revealed a trace of 45-mer amplification products from Reaction II. Although the neighboring lanes prevented densitometric quantitation of the 45-mer amplification products from Reaction II, the quantity of 45-mer product was visually estimated to be approximately 0.4 femtomole. This contrasts sharply with the approximate 14 femtomoles of 30-mer blunt product which resulted from the ten cycle amplification using two pairs of probes (Example 3). Thus, the use of three pairs of probes in the amplification procedure provided an approximate 35-fold benefit in signal to noise ratio over the use of two pairs of probes.

EXAMPLE 6

Detection Procedure Using One Labeled Detection Probe

Two reactions were set up to demonstrate the detection system of the present invention using one labeled detection probe and enzymatic ligation of the detection probes to produce a ligated detection product. The variable reactants were established as follows:

Amount of Amplification Product

| Reaction I: | 10.0 femtomoles $AS_{1-3}{}'$ |
| Reaction II: | 1000 femtomoles $AP_2{}'$ |

Additional reagents:

Ligase/NAD reagent was prepared the same as in Example 5.

EDTA/dye reagent was prepared to contain 20 mM EDTA, 6.1 M urea, 0.02% bromophenol blue, and 0.02% xylene cyanole.

Detection probe $DP_2$ was phosphorylated with $\gamma$-$^{32}P$-ATP and polynucleotide kinase (Boehringer Mannheim Biochemicals, Indianapolis, Ind.) to a specific activity of approximately 7000 Ci/mmole.

Both Reaction I and Reaction II were started in a volume of 23 µL, 1.09× in ELB, with 100 femtomoles of each of detection probes $DP_1$ and $^{32}P\text{-}DP_2$ being added to the two reaction mixtures.

Figure 6:
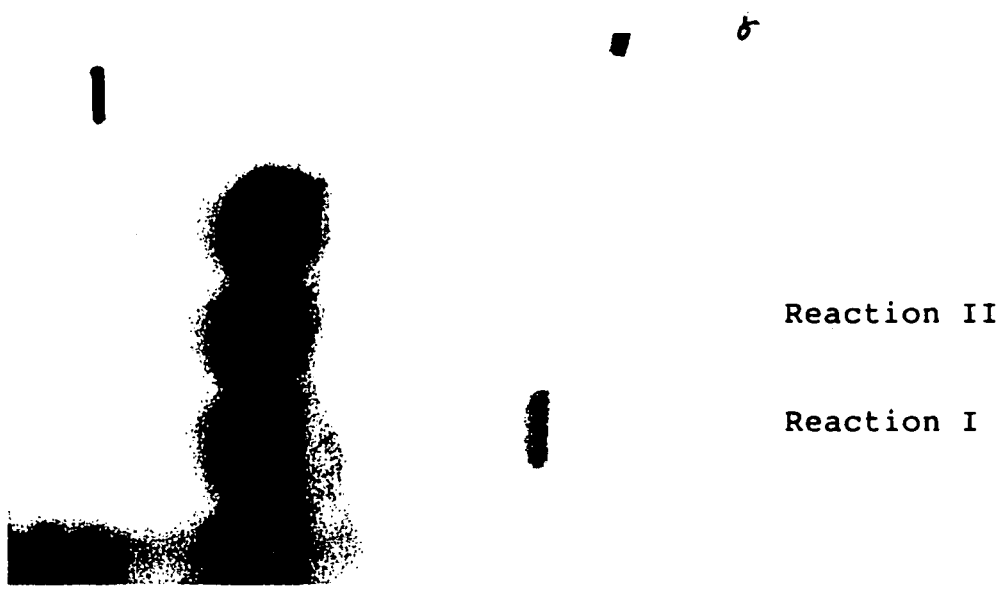
FIG. 6 is an autoradiogram illustrating the detection product obtained using one radio-labeled detection probe in combination with one non-labeled detection probe to detect a 45-mer amplification product.

The reaction mixtures were incubated at 90° C. for 5 minutes, and then allowed to anneal at room temperature for 15 minutes. Two (2.0) µL of Ligase/NAD reagent was added to each polypropylene microtube, and the contents mixed by light agitation. Ligation was allowed to proceed for 5 minutes at room temperature to complete formation of the detection product. The reactions were quenched by the addition of 25 µL of EDTA/dye reagent. This was followed by heating to 90° C. for 5 minutes, and subsequent quick chilling on ice. The radioactive products were separated by running the reaction mixtures on denaturing 15% PAGE and visualized by autoradiography (FIG. 6). Reaction I produced the expected 30-mer detection product. There was no sign of ligated material in Reaction II.

EXAMPLE 7

Labeling of Probes with Fluorescein

Amplification probe $AP_1$ was labeled at its 5'-end with fluorescein using a two-step process, with an amine group first being attached during synthesis using a 5'-Amino-Modifier C6 (Glen Research Corporation, Herndon, Va.) as the last cycle of synthesis. B. A. Connolly, *Nucleic Acids Res.*, 15, 3131 (1987). The 5'-amino modifier is a β-cyanoethyl phosphoramidite which, when activated (e.g., with 1H-tetrazole) couples with the 5'-terminus of the oligonucleotide in a manner similar to the coupling of a nucleoside phosphoramidite with the oligonucleotide. The primary amine group is protected with a monomethoxy-trityl group which is subsequently removed in the deprotection cycle using trichloroacetic acid. After coupling, oxidation, deprotection, and removal of the oligo-amine from the support (as described in Example 1), fluorescein was attached as described below.

Four (4.0) O.D. units of crude oligonucleotide were evaporated to dryness in a SpeedVac® Evaporator (Savant Instruments, Inc., Farmingdale, N.Y.). A 50 µl aliquot of 80% ethanol was then added to the residue, after which the sample was again evaporated. The crude oligo-amine residue was dissolved in 25 µl of 100 mM sodium bicarbonate/sodium carbonate ($NaHCO_3/Na_2CO_3$) buffer adjusted to a pH of 9.5. To this was added 25 µl of a solution of FITC (Aldrich Chemical Company, Inc., Milwaukee, Wis.) in DMSO at a concentration of 10.0 mg/ml. The resulting mixture was vortexed for a few seconds, then centrifuged for a few seconds, and allowed to react in the dark for 15 min. at room temperature.

In order to maximize the yield of fluorescein-labeled oligonucleotide, the reaction was repeatedly exposed to FITC by adding another 25 µl of $NaHCO_3/Na_2CO_3$ buffer (pH 9.5) and another 25 µl of FITC solution in DMSO (10 mg/ml). The reaction was allowed to proceed an additional 15 minutes at room temperature. This was repeated two more times, with the exception that on the last treatment, the reaction was allowed to proceed for 1.5 hour rather than 15 minutes.

The fluorescein-labeled product was precipitated by adding 22 µl of 3M NaOAc and 900 µl of 100% ethanol, followed by cooling at −20° C. for 20 minutes, then centrifugation at 4° C. for 20 minutes, and, finally, decantation of the supernatant. The precipitated product was then washed with 150 µl of 80% ethanol, dried briefly under vacuum, and resuspended in 50 µl of loading (denaturing) buffer (6.3 M urea, 0.02% bromophenol blue, and 0.02% xylene cyanole). The mixture was denatured by boiling for five minutes, then quick chilled in an ice bath, and run on a 15% preparative polyacrylamide gel. The fluoresceinated product was visualized by fluorescence under long wave ultraviolet light, cut from the gel and eluted for 36 hours at room temperature using an elution buffer containing 300 mM NaOAc, 2.5 mM EDTA, and 100 mM Tris.HCl at pH 8.0. The purified product was desalted by passing the supernatant over a G50/50 Sephadex® column (Sigma Chemical Company, St. Louis, Mo.) using 10 mM TEAB as an eluant. Fractions containing oligonucleotide (as determined by U.V. absorption at 260 nm) were combined, evaporated, and resuspended in Tris.HCl/EDTA (10 mM Tris-HCl, 0.1 mM EDTA, pH 8.0). The concentration of the resulting solution was determined by U.V. absorption, with the presence of fluorescein on the oligonucleotide being confirmed by U.V. absorption at 495 nm.

EXAMPLE 8

Detection Procedure Using Two Labeled Detection Probes

Four reactions were set up to demonstrate the detection system of the present invention using two labeled detection probes and enzymatic ligation of the detection probes to produce a ligated detection product. (See, for example, FIG. 2 where the "Ag" is fluorescein and "Ab" is anti-fluorescein antibody.) The variable reactants were established as follows:

Amount of Amplification Product

| Reaction I: | 10 femtomoles $AS_{1\text{-}2}'$ |
|---|---|
| Reaction II: | 1 femtomole $AS_{1\text{-}2}'$ |
| Reaction III: | no $AS_{1\text{-}2}'$ (control) |
| Reaction IV: | 1000 femtomoles $DP_1'$ |

Additional reagents:

Ligase/NAD reagent was prepared at 1× concentration in ELB to contain 130 µM NAD, with 2 µL of the reagent containing 2.0 units of *E. coli* Ligase (New England Biolabs, Inc., Beverly, Mass.).

EDTA/dye reagent was prepared to the same as in Example 6.

Capture buffer, 1× in SSPE and 0.01% in ATC (alkaline-treated casein; Livesay, J. H. and R. A. Donald, *Clin. Chim. Acta*, 123, 193 (1982)), was prepared by dissolving 8.7 g NaCl, 1.38 g $NaH_2PO_4$—$H_2O$ monobasic, 370 mg EDTA, and 100 mg ATC in 800 ml $H_2O$. The solution was adjusted to pH 6.8 with 5 N NaOH, after which the volume was brought up to 1 L.

Amplification probe $AP_2$ was phosphorylated with γ-$^{32}P$-ATP and polynucleotide kinase (Boehringer Mannheim Biochemicals, Indianapolis, Ind.) to a specific activity of approximately 7000 Ci/mmole.

Amplification probe $AP_1$ was labeled with fluorescein on the 5'-end using the procedure described in Example 7.

Magnetic sheep anti-fluorescein microspheres were obtained from Advanced Magnetics, Inc., Cambridge, Mass.

In this example, Fl-$AP_1$ and $^{32}P\text{-}AP_2$ act as detection primers used to measure $AS_{1\text{-}2}'$. $DP_1'$ acts as a potential "bridge".

Each reaction was run in duplicate in a starting volume of 8 µL, with the reaction mixtures being identical in that they contained 100 femtomoles each of Fl-AP$_1$ and $^{32}$P-AP$_2$, and were 1.25× in ELB. All of the reaction mixtures were denatured by incubating the mixtures at 90° C. for 5 minutes, with the nucleic acid sequences then being allowed to anneal at room temperature for 5 minutes. In order to ligate the hybridized detection probes, 2.0 µL of Ligase/NAD reagent was added to each polypropylene microtube and the contents mixed by light agitation. Ligation was allowed to proceed for 5 minutes at room temperature. The ligation reactions were then quenched by the addition of 300 µL of capture buffer.

Magnetic microspheres (beads) coated with anti-fluorescein antibody were placed in 75×12 mm test tubes, with each tube containing 50 µl of the beads. The beads were then washed twice by adding 500 µl of capture buffer and agitating the solutions for several seconds, after which the beads were cleared by placing the wash solutions containing the beads in a Corning Magnetic Separator Unit (Ciba-Corning Diagnostics, Medfield, Mass.) for 5 minutes at room temperature. The aqueous portions of the wash solutions were then pipetted off, leaving the beads in the test tubes.

Each of the quenched reaction mixtures was pipetted into one of the bead-containing test tubes, with the beads allowed to capture the fluorescein-labeled products for a period of about 15 minutes at 50° C., with intermittent agitation. The beads containing fluorescein-labeled product were separated from the supernatant and then washed two times in the same manner in which the anti-fluorescein antibody-coated beads were initially washed. The washed beads containing fluorescein-labeled product were then transferred to polypropylene microtubes by suspending them in 300 µl of capture buffer and pipetting the suspension into the polypropylene microtubes. The samples were counted for one minute using a Beckman LS-6800 liquid scintillation counter. The resulting data is set forth in Table 1.

TABLE I

| Reaction | Variable Contents | Average CPM | Standard Deviation |
|---|---|---|---|
| I | 10 femtomoles AS$_{1-2}$' | 12,065 | ±767 |
| II | 1 femtomole AS$_{1-2}$' | 1,158 | ±28 |
| III | no AS$_{1-2}$' (control) | 63 | ±23 |
| IV | 1000 femtomoles DP$_1$' | 134 | ±28 |

As seen from the data, a linear response, relative to the amount of amplification product present, was obtained from this assay. The presence of a potential "bridge" (Reaction IV) yielded some signal but the amount of signal was minimal as compared to the signal obtained using 1.0 femtomole of amplification product as the target for the detection probes (Reaction II).

Various other examples and modifications of the foregoing description and examples will be apparent to a person skilled in the art after reading the present disclosure without departing from the spirit and scope of the invention, and it is intended that all such examples or modifications be included within the scope of the appended claims.

What is claimed is:

1. A method for detecting an amplification product having three or more ligated amplification probe segments, comprising:
    (a) contacting said amplification product with at least two detection probes wherein at least one of said detection probes is labeled, and wherein each of said detection probes is complementary to a portion of each of two of said ligated amplification probe segments which are adjacently situated in said amplification product;
    (b) allowing each of said detection probes to hybridize to two adjacently situated amplification probe segments of said amplification product with said detection probes binding to said amplification product in a contiguous manner to form a detection product;
    (c) detecting the presence of said detection product through the presence of said label.

2. The method of claim 1 further comprising separating said unhybridized labeled probes from said hybridized product.

3. The method of claim 2 wherein one of said detection probes is labeled with a first proximity label and the other of said detection probes is labeled with a second proximity label.

4. The method of claim 1 wherein;
    (a) said hybridized detection probes are ligated to form a ligated detection product; and,
    (b) detecting the presence of said ligated detection product.

5. The method of claim 4 wherein said hybridized detection probes are joined together by the action of a ligase.

6. The method of claim 5 wherein said ligase is a thermostable ligase.

7. The method of claim 4 wherein said hybridized detection probes are joined together through a chemical reaction.

8. The method of claim 4 wherein one of said detection probes is labeled with a detectable label and the other of said detection probes is labeled with a means for removing said ligated detection product from solution.

9. A method for detecting a target nucleic acid sequence which may be present in a test sample comprising:
    (a) contacting said test sample with an excess of at least three pairs of nucleic acid amplification probes, sufficient to drive the reaction forward wherein the member probes of each of said pairs of amplification probes are complementary to each other and at least one same hybridizing member of each pair of probes is also complementary to an amplification sequence of said target nucleic acid sequence, said amplification sequence acting as a template sequence;
    (b) allowing said hybridizing members of said amplification probes to hybridize to said template sequence, with said amplification probes binding to said amplification sequence in a contiguous manner;
    (c) ligating said hybridized amplification probes to form an amplification product wherein each of said ligated amplification probes forms an amplification probe segment of said amplification product;
    (d) effecting separation of said amplification product from said template sequence;
    (e) repeating steps (a) through (d) wherein said amplification product also acts as a template sequence in subsequent cycles of steps (a) through (d);
    (f) contacting said amplification product with at least two detection probes, wherein at least one of said detection probes is labeled, and wherein each of said detection probes is complementary to a portion of each of two of said amplification probe segments which are adjacently situated in said amplification product;
    (g) allowing each of said detection probes to hybridize to two adjacently situated amplification probe segments of said amplification product, with said detection probes binding to said amplification product in a contiguous manner to form a detection product;
(h) detecting the presence of said hybridized detection product through the presence of said label.

10. The method of claim 9 further comprising:
(a) causing said hybridized detection probes to join together to form a ligated detection product; and,
(b) detecting the presence of said ligated detection product.

11. The method of claim 9 wherein said hybridized amplification probes are joined together by the action of a ligase.

12. The method of claim 10 wherein said ligase is a thermostable ligase.

13. The method of claim 9 wherein said hybridized amplification probes are joined together through a chemical reaction.

14. The method of claim 9 wherein said amplification sequence is contacted with n pairs of amplification probes and said amplification product in contacted with n−1 detection probes.

15. The method of claim 14 wherein said amplification sequence is contacted with 3 pairs of amplification probes and said amplification product in contacted with 2 detection probes.

16. The method of claim 14 wherein said amplification sequence is contacted with 4 pairs of amplification probes and said amplification product in contacted with 3 detection probes.

17. The method of claim 14 wherein said amplification sequence is contacted with 5 pairs of amplification probes and said amplification product in contacted with 4 detection probes.

18. The method of claim 11 wherein said amplification sequence is contacted with n pairs of amplification probes and said amplification product in contacted with n−1 detection probes.

19. The method of claim 18 wherein said amplification sequence is contacted with 3 pairs of amplification probes and said amplification product in contacted with 2 detection probes.

20. The method of claim 18 wherein said amplification sequence is contacted with 4 pairs of amplification probes and said amplification product in contacted with 3 detection probes.

21. The method of claim 18 wherein said amplification sequence is contacted with 5 pairs of amplification probes and said amplification product in contacted with 4 detection probes.

22. The method of claim 12 wherein said amplification sequence is contacted with n pairs of amplification probes and said amplification product in contacted with n−1 detection probes.

23. The method of claim 22 wherein said amplification sequence is contacted with 3 pairs of amplification probes and said amplification product in contacted with 2 detection probes.

24. The method of claim 22 wherein said amplification sequence is contacted with 4 pairs of amplification probes and said amplification product in contacted with 3 detection probes.

25. The method of claim 22 wherein said amplification sequence is contacted with 5 pairs of amplification probes and said amplification product in contracted with 4 detection probes.

* * * * *